United States Patent [19]

Moriyama et al.

[11] Patent Number: 5,229,390
[45] Date of Patent: Jul. 20, 1993

[54] PHYSIOLOGICALLY ACTIVE DIETETIC COMPOSITION

[75] Inventors: Kou Moriyama, Tokyo; Kenji Sato, Osaka, both of Japan

[73] Assignee: Takeda Chemical Industries, Ltd., Osaka, Japan

[21] Appl. No.: 873,761

[22] Filed: Apr. 27, 1992

[30] Foreign Application Priority Data

Apr. 26, 1991 [JP] Japan .................................. 3-124931

[51] Int. Cl.$^5$ ............................................. A61K 31/52
[52] U.S. Cl. .................................... 514/264; 514/296; 426/72
[58] Field of Search .................... 514/264, 276; 426/72

[56] References Cited

U.S. PATENT DOCUMENTS 3,864,469  2/1975  Reiser et al. ........................ 514/276

OTHER PUBLICATIONS

World Patents Index Latest, Week 8851, Derwent Publications Ltd., AN 88-363975 (Nov. 1988).
*Chemical Abstracts*, vol. 115, No. 18, Nov. 4, 1991, Abstract No. 189780M.

Primary Examiner—Marianne M. Cintins
Assistant Examiner—John Peabody
Attorney, Agent, or Firm—Wegner, Cantor, Mueller & Player

[57] ABSTRACT

An edible composition comprising an amino acid capable of accelerating a release of glucagon, known as an adipokinetic hormone, a xanthine derivative capable of degrading body fats, and a thiamine compound essential to caloric metabolism, is provided. The composition is advantageously useful in the enhanced mobilization of depot body fats through physical activities such as sports, work, aerobic movements, jogging, and the like.

6 Claims, No Drawings

PHYSIOLOGICALLY ACTIVE DIETETIC COMPOSITION

FIELD OF THE INVENTION

The present invention relates to an edible composition for keeping fit, specifically, one which is capable of reducing body fats in addition to slimming by exercising. Particularly, the invention relates to a food or beverage comprising at least one amino acid capable of accelerating a release of glucagon, at least one xanthine derivative and at least one thiamine compound, with a dietetically acceptable vehicle.

BACKGROUND OF THE INVENTION

With the development of civilized lives, imbalanced diets lead to obesity, which is a most serious social problem.

Obesity results from excess energy which is stored as depot body fats when caloric intake is greater than caloric consumption. The regimen which has been taken heretofore for the remedy of obesity includes limitation of energy consumed, such as the restriction of sugar intake.

However, the continuous practice of a diet is difficult because such remedies require patience and cause hardship for the dieter.

It has been recently noted that an increase of caloric consumption is important for remedying obesity and dieting. Thus, mainly among youngsters, aerobic kinesitherapy including aerobic movement is actively practiced.

There are carbohydrates and lipids as sources of kinetic energy. For example, carbohydrates are normally stored in only an amount of about 840 Kcal as glycogen in a human body weighting 70 Kg, while lipids are stored in an amount of about 135,000 Kcal as body fat. The preferred remedy for obesity (i.e., the preferred method for slimming) is to maximize the utilization of body fats as the source of kinetic energy, so as to consume more energy by the same movement. For this purpose, it is necessary to increase the amount of free fatty acid (FFA) in blood without augmentation of the blood sugar level.

Prior art diet products such as sports beverages and juices contain too much sugar, however. Thus, the metabolic alterations of fats are inhibited due to an increase of blood sugar level and a decrease of FFA in blood when such products are eaten during exercises.

For these reasons, it is desired to develop a food or beverage capable of utilizing fats efficiently well as enhancing consumption of energy.

SUMMARY OF THE INVENTION

The inventors have succeeded in the preparation of foods and beverages comprising an amino acid capable of accelerating a release of glucagon, known as an adipokinetic hormone, a xanthine derivative capable of degrading body fats, and a thiamine compound essential to caloric metabolism. It has been found that enhanced mobilization of body fats occurs unexpectedly in in vivo examination of such compositions.

The invention relates to an edible composition which comprises at least one amino acid capable of accelerating a release of glucagon, at least one xanthine derivative and at least one thiamine compound.

The invention specifically relates to a food or beverage which comprises at least one amino acid capable of accelerating a release of glucagon, at least one xanthine derivative and at least one thiamine compound.

The mobilization of body fats are activated by the intake of the diet according to the present invention, thereby enhancing the consumption of total calories through exercises and their effects on the remedy for obesity.

The invention also relates to a method for enhancing mobilization of body fats in a mammal which comprises administering an effective amount of the edible composition to said mammal.

DETAILED DESCRIPTION OF THE INVENTION

The invention relates to an edible composition for enhancing mobilization of body fats, specifically for utilizing body fats efficiently or enhancing consumption of energy, which comprises at least one amino acid capable of accelerating a release of glucagon, at least one xanthine derivative and at least one thiamine compound, with a dietetically acceptable vehicle.

The invention also relates to a method for enhancing mobilization of body fats in a mammal which comprises administering (e.g. feeding) an effective amount of the edible composition to said mammal.

The invention still further relates to a method for utilizing body fats efficiently or enhancing consumption of energy, which comprises administering an effective amount of the edible composition to said mammal.

Particularly, the invention relates to a food or beverage comprising at least one amino acid capable of accelerating the release of glucagon, at least one xanthine derivative and at least one thiamine compound, with a dietetically acceptable vehicle, which is capable of reducing body fats in addition to slimming by taking exercises, e.g. without any substantially adverse effect such as a transient increase of blood glucose.

The amino acid capable of accelerating the release of glucagon is not limited, to but may include any of various amino acids capable of accelerating the release of glucagon. Examples of such amino acids include arginine, alanine, leucine, etc. Among them, arginine is preferable. The amino acid may be either in a free form or in a dietetically acceptable salt form. The salts include metal salts such as a sodium salt and a calcium salt, inorganic salts such as hydrochloride, carbonate and sulfate, organic salts such as acetate, malate and succinate, etc.

The xanthine derivatives may include preferably natural xanthine derivatives. Examples of such xanthine derivatives may include caffeine, theophylline, theobromine, etc. Among them, caffeine is preferable.

The thiamine compound may include thiamine (vitamin $B_1$) or a dietetically acceptable salt thereof, as well as various synthetic thiamine derivatives. The salts of thiamine include hydrochloride such as thiamine hydrochloride, nitrate such as thiamine mononitrate, phosphate, etc. The synthetic thiamine derivative may include preferably such a thiol-type thiamine derivative selected from the group consisting of unsymmetrical thiamine organic disulfide derivatives, S-acyl thiamine derivatives, and bisthiamine disulfide derivatives or dietetically acceptable salts thereof, as described in U.S. Pat. No. 3,472,735. The unsymmetrical thiamine organic disulfide derivative may include thiamine propyl disulfide (prosultiamine), thiamine tetrahydrofurfuryl disulfide (fursultiamine), thiamine allyl disulfide, thiamine (7-methoxycarbonyl-3-acetylthioheptyl) disulfide, thiamine 2-hydroxyethyl disulfide, etc. The S-acyl thiamine derivative may include S-benzoylthiamine monophosphate (benfotiamine), O,S-diacetylthiamine, O,S-dibenzoylthiamine, S-acetylthiamine O-monophosphate, O,S-dicarboethoxythiamine (cetotiamine), O,S-cyclocarbothiamine (cytotiamine), etc. The bisthiamine disulfide derivative may include thiamine disulfide, O-benzoylthiamine disulfide, etc. Among the above thiamine compounds, thiamine hydrochloride, thiamine mononitrate, thiamine tetrahydrofurfuryl disulfide, O-benzoylthiamine disulfide and S-benzoylthiamine monophosphate are preferable.

The ratio by weight of the amino acid capable of accelerating the release of glucagon: the xanthine derivative: the thiamine compound ranges from 1:0.0001 to 1:0.0001 to 0.1, preferably 1:0.001 to 0.5:0.001 to 0.05, most preferably 1:0.01 to 0.2:0.002 to 0.02.

The food and beverage according to the present invention may contain various dietetically acceptable vehicles and/or additives in addition to the above-mentioned essential ingredients (i.e. the amino acid capable of accelerating the release of glucagon, the xanthine derivative and the thiamine compound, depending on necessity).

Any dietetically acceptable vehicles may be used as long as they have no adverse influence on the acceleration of the glucagon release or the enhanced mobilization of body fats. Examples of such vehicles may include various carriers, extenders, diluting agents, bulking agents, dispersing agents, excipients, binding agents, solvents (e.g. water, ethanol, plant oil, etc.), solution adjuvants, buffering agents, solubilizers, gelling agents (e.g. sodium CMC, HPMC, MC, sodium arginate, etc.), emulsifying agents (e.g. sodium CMC, HPMC, etc.), suspending agents (e.g. sodium CMC, MC, sodium arginate, etc.), etc.

Any dietetically acceptable additives may be used as long as they have no adverse influence on the acceleration of the glucagon release or the enhanced mobilization of body fats. Examples of such additives may include various vitamins (e.g. vitamin A, vitamin $B_2$, vitamin $B_6$, panthothenic acid, nicotinic acid, vitamin C, vitamin E, etc.), sweetening agents, organic acids (e.g. citric acid, malic acid, fumaric acid, malonic acid, succinic acid, tartaric acid, lactic acid, etc.), coloring agents, flavoring agents (e.g. vanillin, linalool, natural perfumes, etc.), anti-wetting agents, fibers, electrolytes, minerals, nutrients, antioxidants, preservatives, aromas, humectants, natural plant extracts (e.g. tea extracts, coffee extracts, cocoa extracts, fruit extracts such as orange, grape, apple, peach, pineapple, pear, plum, cherry, papaya, tomato, melon, strawberry, and raspberry, etc.), etc.

The food and beverage according to the present invention are preferably those substantially free from a caloric sweetening agent such as sucrose, fructose, glucose and the like. More preferably, the food and beverage are sweetened with a non-sugar sweetening agent. Such non-sugar sweetening agents include aspartame, stevia and saccharin.

The food and beverage according to the present invention may be in various forms suitable for beverages or non-beverages, and beverages are more preferable.

The food and beverage according to the present invention may be formulated or prepared by conventional methods for the preparation of foods and beverages including diets, pharmaceuticals, canned foods, juices, syrups, etc. For example, a determined amount of the essential ingredients of the present invention and, depending on necessity, the above-mentioned vehicles and/or additives, is dissolved in a suitable diluting agent (e.g. water) to form the subject beverage.

The proportion of the essential ingredient in the final product according to the present invention is not limited to but is suitably about 0.1 to 25 g, preferably 0.5 to 15 g, most preferably 1 to 10 g per total 100 g of the final beverage product. The proportion of the additive in the final product according to the present invention is not limited to but is suitably about 0.1 to 10 g, preferably 0.2 to 5 g, most preferably 0.3 to 3 g per total 100 g of the final beverage product.

The beverage according to the present invention may be in a carbonated form for beverages.

The beverage according to the present invention may be in a powder form suitable for immediate preparation before drinking.

Examples of such non-beverages may include various forms such as candies, drops, chocolates, jellies, biscuits, yogurt, and sweets. The non-beverage may be prepared by blending and formulating a determined amount of the essential ingredients and, depending on necessity, the above-mentioned additives, or by blending and formulating them optionally in admixture with a suitable vehicle.

Examples of such vehicles may include flour powder, rice powder, starch powder, cornstarch, polysaccharide, milk protein, collagen, rice oil, lecithin, etc.

The proportion of the essential ingredient in the final product according to the present invention is not limited to but is suitably about 0.1 to 25 g, preferably 0.5 to 15 g, most preferably 1 to 10 g per total 100 g of the final non-beverage product. The proportion of the additive in the final product according to the present invention is not limited to but is suitably about 0.1 to 10 g, preferably 0.2 to 5 g, most preferably 0.3 to 3 g per total 100 g of the final non-beverage product.

The edible compositions according to the present invention have unexpected advantages in the field of diets. The edible compositions according to the present invention are advantageously active in reduction of depot body fats whenever they are consumed, particularly more active upon their intake prior to or during exercises such as sports, physical activities.

The edible compositions according to the present invention are effective in the enhanced mobilization of body fats, as described hereinbelow in Test Examples 1 to 2.

The composition may be used in the remedy of obesity and as a dieting agent. In addition, the combination of practising physical activities such as sports, work and the like and consumption of the present composition is more effective for such remedy.

EXAMPLE 1

1. Formulation of Beverage

TABLE 1

|  | Formulation | | |
| --- | --- | --- | --- |
|  | 1 | 2 | 3 |
| Arginine | 1.2 g | 3 g | 2 g |
| Alanine | — | — | 1 g |
| Caffeine | 50 mg | 100 mg | 80 mg |
| Thiamine mononitrate | 5 mg | 10 mg | 5 mg |
| Citric acid | 1.2 g | 0.8 g | 0.6 g |
| Sodium citrate | 0.3 g | 0.2 g | 0.2 g |

TABLE 1-continued

|  | Formulation | | |
|---|---|---|---|
|  | 1 | 2 | 3 |
| Vitamin $B_2$ | — | 2 mg | 5 mg |
| Vitamin $B_6$ | — | 5 mg | 5 mg |
| Panthothenic acid | — | 10 mg | 20 mg |
| Nicotinic acid | — | 20 mg | 50 mg |
| Maltitol | — | 5 g | 5 g |
| Saccharin | — | — | 20 mg |
| Aspartame | 80 mg | 60 mg | — |
| Flavoring agent | 50 μl | 50 μl | 50 μl |
| Water |  |  |  |
| Total volume | 100 ml | 100 ml | 100 ml |

2. Preparation of Beverage

Each ingredient of Formulation 1 was added to 50 ml of water under stirring and dissolved. The total volume amounted to 100 ml by addition of water.

3. Clinical Test

Normal adult volunteers (6 men: 23 to 28 years old) were divided into 2 groups:

① the beverage of the present invention (Formulation 1) prepared in the above-mentioned Preparation (3 persons), and ② reference beverage A (citric acid: 1.2 g, sodium citrate: 0.3 g, thiamine mononitrate: 5 mg, sorbit: 3 g, aspartame: 80 mg, and flavoring agents: a suitable amount) were dissolved in water to give 100 ml of the beverage) (3 persons).

Each volunteer had the identical dinner prior to the test and, until the next day, foods were prohibited. The volunteer had a breakfast consisting of bread and butter, boiled eggs and milk from A.M. 7:00 until A.M. 7:30, provided that the caloric intake is controlled to 400 Kcal per 60 Kg body weight.

Foods and exercises were prohibited until the test started at A.M. 10:00. After measurement of gas metabolism and collection of blood during a rest, the volunteers had the beverages. The clinical trial was carried out blind (double-blind crossover trial in which neither the tested person nor the investigator is made aware of treatment administered). The tested person had the beverage (100 ml) 30 minutes (−30 min.) prior to the start of test (0 min.). The term of physical exercises was from 0 min. to +45 min. (loaded exercise time). The exercises were carried out at a loaded strength of 40% $VO_2$ max by means of a bicycle ergometer. The following items: plasma adrenaline, plasma noradrenaline, serum growth hormone, serum glucagon, serum insulin, blood glucose, serum free fatty acid, serum neutral fat, blood lactate, heart rate, blood pressure, oxygen consumption, $CO_2$ production, respiratory quotient, and fatigue feeling, were monitored. The term for the measurement was from −40 min. to +150 min. After a two day rest interval, the test was repeated. The three persons who had had the beverage of the present invention at the first trial had the reference beverage at the second trial while the three persons who had had the reference had the beverage of the present invention at the second trial.

4. Result of Clinical Test

Each average and standard deviation with regard to the monitored items was calculated for the beverage of the present invention and the reference. It has been found that there are differences in the serum adrenaline, serum insulin, and serum free fatty acid among the monitored items between the beverage of the present invention and the reference. The results are summarized in Tables 3 to 5 below.

EXAMPLE 2

1. Formulation of Beverage

TABLE 2

|  | Formulation | |
|---|---|---|
|  | B (Reference) | 4 |
| L-Arginine | 6.25 g | 6.25 g |
| Caffeine (anhydrous) | 62.5 mg | 62.5 mg |
| Fursultiamine hydrochloride | — | 125 mg |
| Citric acid | Suitable Amount | Suitable Amount |
| Water |  |  |
| Total volume | 100 ml | 100 ml |

The formulation was adjusted to pH about 6.7 to 6.9 by addition of citric acid.

2. Test

Ten SD rats (5 week old) which had commercially available feeds (CE-2, Nippon Kurea Co. Ltd., Japan) twice a day were divided into 2 groups:

① the beverage of the present invention (Formulation 4) and

② reference beverage (Formulation B).

Each group received 8 ml of the drink (as shown in Table 5) per Kg body weight by oral administration. The oxygen consumption and respiratory quotient (RQ) were measured under rest condition prior to or 30 and 60 minutes later after the administration.

3. Result of Test

Each average and standard deviation with regard to the monitored items was calculated for the beverage of the present invention and the reference. It has been found that there are differences in the respiratory quotient among the monitored items between the beverage of the present invention and the reference while the oxygen consumption was not substantially different. It is clear that the respiratory quotient is decreased after the oral administration of the beverage of the invention. This is interpreted as indicating that metabolism of fatty acid is increased. The results are summarized in Tables 6 and 7.

TABLE 3

| Beverage | Subject | Plasma Adrenaline (ng/ml) Time (min.) | | | | | | |
|---|---|---|---|---|---|---|---|---|
|  |  | 0 | 30 | 75 | 90 | 120 | 150 | 180 |
| The Invention (1) | 1 | 0 | 0.03 | 0.05 | 0.05 | 0 | 0.03 | 0.02 |
|  | 2 | 0 | 0.02 | 0.05 | 0.02 | 0.06 | 0 | 0 |
|  | 3 | 0 | 0.01 | −0.01 | −0.02 | −0.02 | −0.05 | 0.01 |
|  | 4 | 0 | 0 | 0.12 | 0.05 | 0.04 | 0.03 | 0.01 |
|  | 5 | 0 | 0 | 0.05 | 0.02 | 0.05 | 0.01 | 0.02 |
|  | 6 | 0 | 0 | 0.04 | 0.08 | 0.04 | 0.03 | 0 |
|  | Average | 0.00 | 0.01 | 0.05 | 0.03 | 0.03 | 0.01 | 0.01 |
|  | Standard Deviation | 0.00 | 0.01 | 0.04 | 0.03 | 0.03 | 0.03 | 0.01 |
| Reference | 1 | 0 | −0.01 | 0.01 | 0.01 | −0.02 | −0.02 | −0.02 |

TABLE 3-continued

Plasma Adrenaline (ng/ml)

| Beverage | Subject | 0 | 30 | 75 | 90 | 120 | 150 | 180 |
|---|---|---|---|---|---|---|---|---|
| (A) | 2 | 0 | −0.01 | 0.01 | −0.06 | −0.03 | −0.03 | −0.05 |
| | 3 | 0 | −0.03 | 0.03 | −0.03 | −0.03 | −0.03 | −0.03 |
| | 4 | 0 | 0.02 | 0.13 | 0.04 | 0.02 | 0.06 | 0.04 |
| | 5 | 0 | −0.02 | −0.05 | −0.06 | −0.05 | −0.05 | −0.04 |
| | 6 | 0 | 0.01 | 0.06 | 0.06 | 0.06 | 0.02 | 0.03 |
| | Average | 0.00 | −0.01 | 0.03 | −0.01 | −0.01 | −0.01 | −0.01 |
| | Standard Deviation | 0.00 | 0.02 | 0.06 | 0.05 | 0.04 | 0.04 | 0.04 |

TABLE 4

Serum Free Fatty Acid (mEq/l)

| Beverage | Subject | 0 | 30 | 75 | 90 | 120 | 150 | 180 |
|---|---|---|---|---|---|---|---|---|
| The Invention (1) | 1 | 0 | 0.11 | 0.15 | 2.14 | 0.1 | 0.09 | 0.06 |
| | 2 | 0 | 0.11 | 0.06 | 0.24 | 0.03 | 0.1 | 0.15 |
| | 3 | 0 | 0.09 | 0.61 | 0.6 | 0.41 | 0.42 | 0.3 |
| | 4 | 0 | 0.05 | 0.39 | 0.78 | 0.31 | 0.3 | 0.3 |
| | 5 | 0 | 0.02 | 0.33 | 0.53 | 0.09 | 0.14 | 0.17 |
| | 6 | 0 | 0.01 | 0.1 | 0.34 | 0.01 | 0.07 | 0.15 |
| | Average | 0.00 | 0.07 | 0.27 | 0.77 | 0.16 | 0.19 | 0.19 |
| | Standard Deviation | 0.00 | 0.04 | 0.21 | 0.70 | 0.16 | 0.14 | 0.09 |
| Reference (A) | 1 | 0 | 0.07 | 0 | 0.11 | −0.05 | 0.02 | 0.29 |
| | 2 | 0 | 0 | 0.17 | 0.92 | 0.13 | 0.11 | 0.12 |
| | 3 | 0 | −0.03 | 0.24 | 0.5 | 0.17 | 0.21 | 0.22 |
| | 4 | 0 | 0.02 | 0.39 | 0.46 | 0.46 | 0.63 | 0.61 |
| | 5 | 0 | 0 | 0.38 | 1.03 | 0.45 | 0.47 | 0.38 |
| | 6 | 0 | 0.09 | 0.02 | 0.44 | 0.02 | 0.23 | 0.11 |
| | Average | 0.00 | 0.03 | 0.20 | 0.58 | 0.20 | 0.28 | 0.29 |
| | Standard Deviation | 0.00 | 0.05 | 0.17 | 0.34 | 0.21 | 0.23 | 0.19 |

TABLE 5

Serum Insulin (μU/ml)

| Beverage | Subject | 0 | 30 | 75 | 90 | 120 | 150 | 180 |
|---|---|---|---|---|---|---|---|---|
| The Invention (1) | 1 | 0 | 2 | −1 | 1 | 0 | 1 | 1 |
| | 2 | 0 | −1 | −1 | −1 | 0 | −1 | −1 |
| | 3 | 0 | 1 | 1 | −1 | −1 | 1 | 0 |
| | 4 | 0 | −4 | −4 | −3 | −2 | −3 | −3 |
| | 5 | 0 | −1 | −1 | −1 | −1 | −1 | −1 |
| | 6 | 0 | 0 | 1 | 0 | 0 | 0 | 0 |
| | Average | 0.00 | −0.50 | −0.83 | 0.83 | −0.67 | −0.50 | 0.67 |
| | Standard Deviation | 0.00 | 2.07 | 1.83 | 1.33 | 0.82 | 1.52 | 1.37 |
| Reference (A) | 1 | 0 | 0 | −1 | −1 | −1 | 0 | −1 |
| | 2 | 0 | −4 | −4 | −3 | −6 | −6 | −5 |
| | 3 | 0 | −3 | −5 | −5 | −4 | −4 | −5 |
| | 4 | 0 | 1 | −1 | 0 | 0 | 0 | −1 |
| | 5 | 0 | 0 | 0 | 1 | 1 | 0 | 0 |
| | 6 | 0 | 1 | 0 | 1 | 0 | 0 | 0 |
| | Average | 0.00 | −0.83 | −1.83 | −1.17 | −1.67 | −1.67 | −2.00 |
| | Standard Deviation | 0.00 | 2.14 | 2.14 | 2.40 | 2.73 | 2.66 | 2.37 |

TABLE 6

Respiratory Quotient (RQ)

| | | Administration | | |
|---|---|---|---|---|
| Beverage | Subject | Before | 30 min. later | 90 min. later |
| The Invention (4) | 1 | 0.73 | 0.79 | 0.72 |
| | 2 | 0.68 | 0.69 | 0.71 |
| | 3 | 0.72 | 0.70 | 0.64 |
| | 4 | 0.79 | 0.80 | 0.75 |
| | 5 | 0.73 | 0.73 | 0.77 |
| | Average | 0.73 | 0.74 | 0.72 |
| | Standard Deviation | 0.039 | 0.051 | 0.050 |
| Reference (B) | 1 | 0.74 | 0.69 | 0.79 |
| | 2 | 0.79 | 0.77 | 0.75 |
| | 3 | 0.70 | 0.76 | 0.74 |
| | 4 | 0.76 | 0.75 | 0.79 |
| | 5 | 0.81 | 0.76 | 0.82 |
| | Average | 0.76 | 0.75 | 0.78 |
| | Standard Deviation | 0.043 | 0.029 | 0.033 |

TABLE 7

Oxygen Consumption

| | | Administration | | |
|---|---|---|---|---|
| Beverage | Subject | Before | 30 min. later | 90 min. later |
| The Invention (4) | 1 | 46.68 | 46.10 | 46.27 |
| | 2 | 48.01 | 48.51 | 41.91 |
| | 3 | 44.15 | 44.08 | 44.37 |
| | 4 | 48.58 | 53.52 | 54.12 |
| | 5 | 53.32 | 53.21 | 53.36 |
| | Average | 48.1 | 49.1 | 48.0 |

TABLE 7-continued

| Beverage | Subject | Oxygen Consumption | | |
|---|---|---|---|---|
| | | Administration | | |
| | | Before | 30 min. later | 90 min. later |
| | Standard Deviation | 3.36 | 4.21 | 5.46 |
| Reference (B) | 1 | 43.05 | 51.14 | 44.44 |
| | 2 | 46.94 | 47.30 | 47.08 |
| | 3 | 45.86 | 45.51 | 39.62 |
| | 4 | 49.46 | 56.04 | 54.84 |
| | 5 | 50.81 | 50.82 | 50.23 |
| | Average | 47.2 | 50.2 | 47.2 |
| | Standard Deviation | 3.05 | 4.06 | 5.76 |

What is claimed is:

1. A physiologically active dietetic composition which comprises (a) a member selected from the group consisting of arginine, alanine, leucine, a dietetically acceptable salt thereof and a mixture thereof, (b) a member selected from the group consisting of caffeine, theophylline, theobromine and a mixture thereof and (c) a member selected from the group consisting of thiamine, thiamine tetrahydrofurfuryl disulfide, O-benzoylthiamine disulfide, S-benzoylthiamine monophosphate, a dietetically acceptable salt thereof and a mixture thereof, together with a dietetically acceptable vehicle, the ratio by weight of (a):(b):(c) being 1:0.0001 to 1:0.0001 to 0.1.

2. The physiologically active dietetic composition according to claim 1, wherein the ratio by weight of (a):(b):(c) is 1:0.001 to 0.5:0.001 to 0.05.

3. The physiologically active dietetic composition according to claim 1, which is in the form of a beverage.

4. The physiologically active dietetic composition according to claim 1, wherein the component (c) is thiamine hydrochloride or thiamine mononitrate.

5. The physiologically active dietetic composition according to claim 1, which is substantially free from a caloric sweetening agent.

6. The physiologically active dietetic composition according to claim 1, which is a beverage comprising arginine as component (a), caffeine as component (b) and thiamine mononitrate as component (c).

* * * * *